US008461211B2

(12) United States Patent
Bauer et al.

(10) Patent No.: US 8,461,211 B2
(45) Date of Patent: *Jun. 11, 2013

(54) USE FOR BUDESONIDE AND FORMOTEROL

(75) Inventors: Carl-Axel Bauer, Lund (SE); Jan Trofast, Lund (SE)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 12/982,360

(22) Filed: Dec. 30, 2010

(65) Prior Publication Data

US 2011/0097282 A1  Apr. 28, 2011

Related U.S. Application Data

(63) Continuation of application No. 10/010,283, filed on Nov. 13, 2001, now Pat. No. 7,897,646, which is a continuation of application No. 09/670,457, filed on Sep. 26, 2000, now abandoned, which is a continuation of application No. 09/194,290, filed as application No. PCT/SE98/01599 on Sep. 9, 1998, now abandoned.

(30) Foreign Application Priority Data

Sep. 19, 1997 (SE) ..................................... 9703407

(51) Int. Cl.
*A61K 31/56* (2006.01)
*A61K 31/16* (2006.01)
*A61K 9/12* (2006.01)

(52) U.S. Cl.
USPC .............................. 514/630; 514/171; 424/45

(58) Field of Classification Search
USPC ..................................... 514/630, 171; 424/45
See application file for complete search history.

(56) References Cited

U.S. PATENT DOCUMENTS

| 5,250,286 | A | 10/1993 | Skupin |
| 5,684,199 | A | 11/1997 | Francotte |
| 5,795,564 | A | 8/1998 | Aberg et al. |
| 5,983,956 | A | 11/1999 | Trofast |
| 5,996,576 | A | 12/1999 | Yule |
| 7,897,646 | B2 * | 3/2011 | Bauer et al. ................ 514/630 |

FOREIGN PATENT DOCUMENTS

| CA | 2123909 | 6/1993 |
| CA | 2356145 | 6/1993 |
| EP | 0 416 950 A1 | 3/1991 |
| EP | 0 416 951 A1 | 3/1991 |
| EP | 0 523 638 | 1/1993 |
| EP | 1085877 | 12/1999 |
| EP | 1 014 993 | 7/2000 |
| EP | 0613371 | 3/2002 |
| SE | 9703407-8 | 9/1998 |
| WO | WO 92/11280 | 7/1992 |
| WO | WO 93/11773 | 6/1993 |
| WO | WO 97/11783 | 4/1997 |
| WO | WO 98/15280 | 4/1998 |
| WO | WO 98/31351 | 7/1998 |
| WO | WO 99/00134 | 1/1999 |
| WO | WO 99/64014 | 12/1999 |
| WO | WO 00/30608 | 6/2000 |
| WO | WO 00/35441 | 6/2000 |
| WO | WO 00/53188 | 9/2000 |

OTHER PUBLICATIONS

Affidavit of Jan William Trofast, before the Opposition Board, Patent Office, Delhi; submitted on behalf of AstraZeneca, dated Sep. 13, 2006 (7 pages).
"American Thoracic Society: Standards for the Diagnosis and Care of Patients with Chronic Obstructive Pulmonary Disease," *Am. J. Respir. Care Med.* 152:S77-S121 (1995).
Ankerst et al., "Tolerability of a High Dose of Budesonide/Formoterol in a Single Inhaler in Patients with Asthma," manuscript (24 pages), as submitted for publication to Pulm. Pharm. Ther. with letter dated Feb. 6, 2003 to the EPO, later published as vol. 16(3), pp. 147-151 (2003).
Arvidsson et al., "Inhaled formoterol during one year in asthma: a comparison with salbutamol," Eur Respir J, 4:1168-1173, 1991.
"Atemstillstand" Pschyrembel Klinisches Wörtebuch (2002) (in German).
Aubier et al., "Salmeterol/Fluticasone propionate (50/500 μg) in combination in a Diskus® inhaler (Seretide®) is effective and safe in the treatment of steroid-dependent asthma," Respir. Med. 93:876-884, 1999.
Auffarth et al., "Effects of inhaled budesonide on spirometric values, reversibility, airway responsiveness, and cough threshold in smokers with chronic obstructive lung disease" Thorax 46:372-377 (1991).
Barnes et al., "Chronic obstructive pulmonary disease: molecular and cellular mechanisms," *Eur. Respir. J.* 22:672-688 (2003).
Barnes, "A Single Inhaler for Asthma?," American Journal of Respiratory and Critical Care Medicine, vol. 171, pp. 95-96 (2005).
Barnes, "Inhaled steroids in COPD" *The Lancet* 351:766-767 (1998).
Barnes, "A New Approach to the Treatment of Asthma," Drug Therapy, vol. 321(22), pp. 1517-1527 (2002).
Barnes, "Chronic Obstructive Pulmonary Disease," Medical Progress, vol. 343(4), pp. 269-280 (2000).
Barnes, "Inhaled steroids in COPD," The Lancet, vol. 351, pp. 766-767 (1998).
Bartow et al., "Formoterol: An Update of its Pharmacological Properties and Therapeutic Efficacy in the Management of Asthma," Drugs, 55(2):303-322, 1998.
Basic Reference Manual, vol. 1, revised ed. of 1988, issued by IMS International.
Bateman et al, "Overall asthma control: The relationship between current control and future risk," J. Allergy Clin. Immunol., vol. 125(3), pp. 600-608e6 (2010).
Bjermer et al., "Long-acting β2-agonists: how they are used in an optimal way?," Respiratory Medicine, vol. 91, pp. 587-591 (1997).
Bond, "A strategy that works," New Zealand Medical Journal, p. 369, Aug. 28, 1991.
"The British Guidelines on Asthma Management 1995 Review and Position Statement," Thorax, 52(Suppl 1):S1-21, 1997.
Bousquet et al., "Budesonide/formoterol for maintenance and relief in uncontrolled asthma vs. high-dose salmeterol/fluticasone," Respiratory Medicine, vol. 101, pp. 2437-2446 (2007).
Boyd et al., "An Evaluation of Salmeterol in the Treatment of Chronic Obstructive Pulmonary Disease (COPD)," Eur. Resp. J. 10:815-821 (1997).

(Continued)

*Primary Examiner* — Jennifer M Kim
(74) *Attorney, Agent, or Firm* — Fish & Richardson P.C.

(57) ABSTRACT

The invention provides the use of formoterol and budesonide in the treatment of chronic obstructive pulmonary disease.

20 Claims, No Drawings

OTHER PUBLICATIONS

"Bronchodilators and anti-inflammatories," Monthly Index of Medical Specialities (MIMS) 242-256 (Sep. 1997).
Buist, "Definitions," in *Asthma and Chronic Obstructive Pulmonary Disease*, Barnes et al. eds., Acad. Press, pp. 3-6 (2002).
BTS Guidelines for the Management of Chronic Obstructive Pulmonary Disease, Thorax, vol. 52(a), pp. S1-S28 (1997).
Bourbeau et al., "Randomised controlled trial of inhaled corticosteroids in patients with chronic obstructive pulmonary disease," Thorax, vol. 53, pp. 477-482 (1998).
Burge et al. "Randomised, double blind, placebo controlled study of fluticasone propionate in patients with moderate to severe chronic obstructive pulmonary disease: the ISOLDE trial," British Med. J. 320:1297-1303 (2000).
Calverley et al., "Preventing mortality in COPD: The value of inhaled budesonide added to bronchodilators." Presentation at COPD5, Birmingham, UK, Jun. 28, 2006, Abstract 35.
Calverley et al., "Maintenance therapy with budesonide and formoterol in chronic obstructive pulmonary disease," *Eur. Respir. J.* 22:912-919 (2003).
Cates et al. "Combination formoterol and budesonide as maintenance and reliever therapy versus inhaled steroid maintenance for chronic asthma in adults and children (Review)," Published by Wiley and Sons, Ltd., 64 pages. (2010).
Chapman, "SMART isn't," J. Allergy Clin Immunol., vol. 125, pp. 609-610 (2010).
Chapter 2, Six-Part Asthma Management Program (International Consensus Report on Diagnosis and Management of Asthma), Allergy, vol. 47, suppl. 13, pp. 6-49 (1992).
Clinical Practice Guidelines, Expert Panel Report 2, Guidelines for the Diagnosis and Management of Asthma, NIH Publication No. 97-4051, Jul. 1997.
Cochrane, "Bronchial asthma and the role of $\beta_2$ agonists" in *Formoterol, a new generation $\beta_2$ agonist*: an international symposium held during the $8^{th}$ Congress of the European Society of Pneumology, Freiburg, Federal Republic of Germany, Sep. 1989, Editors Peter J. Barnes and Heinrich Matthys, published by Hogrefe and Huber Publishers, Toronto 1990, at pp. 24-30.
Collins et al., "The Use of Corticosteroids in the Treatment of Acute Asthma," Quarterly Journal of Medicine, New Series, XLIV:259-73, 1975.
Compendium Suisse des Medicaments, 15th Ed. 1997/1998, Ed. Grand Public, compiled Jun. 1996, pp. 2-3, 419-420, 866 (in French).
Compendium Suisse des Medicaments, 18th Ed. 1997, compiled Jun. 1996, pp. 5, 849-851 and 1635-1636 (in French).
Corden and Rees, "The effect of oral corticosteroids on bronchodilator responses in COPD," Respiratory Medicine, vol. 92, pp. 279-282 (1998).
Corren et al., "Twelve-Week, Randomized, Placebo-Controlled, Multicenter Study of the Efficacy and Tolerability of Budesonide and Formoterol in One Metered-Dose Inhaler Compared with Budesonide Alone and Formoterol Alone in Adolescents and Adults with Asthma," Clinical Therapeutics, 29(5):823-843, 2007.
Costain et al., "Guidelines for management of asthma in adults: I—chronic persistent asthma," BMJ, 301:651-653, 1990.
Dalby et al., "The bioavailability and airway clearance of the steroid component of budesonide/formoterol and salmeterol/fluticasone after inhaled administration in patients with COPD and healthy subjects: a randomized controlled trial," Respiratory Research, vol. 10(104), pp. 1-11 (2009).
Davies et al., "Oral corticosteroid trials in the management of stable chronic obstructive pulmonary disease," Q. J. Med. 92:395-400 (1999).
Decision of the EPO Opposition Division regarding patent EP-B-1210943, dated Dec. 5, 2008.
Declaration of Professor N. B. Pride dated Aug. 4, 2004.
Definitions, Epidemiology, Pathophysiology, Diagnosis, and Staging, American Journal of Respiratory and Critical Care Medicine, vol. 152, pp. S78-S121 (1995).
Devidayal et al., "Efficacy of nebulized budesonide compared to oral prednisolone in acute bronchial asthma," Acta Paediatr, 88:835-840, 1999.

"Disorders of the Airways," Current Medical Diagnosis and Treatment 1997 36th ed. pp. 241-255, Stamford, CT: Appleton and Lange (1997).
Dompeling et al., "Slowing the deterioration of Asthma and Chronic Obstructive Pulmonary Disease Observed during Bronchodilator Therapy by Adding Inhaled Corticosteroids," Ann. Intern. Med. 118(10):770-778 (1993).
D'Urzo, "Inhaled Glucocorticosteroid and Long-Acting $\beta2$-Adrenoceptor Agonist Single-Inhaler Combination for Both Maintenance and Rescue Therapy," Treat Respir Med 5:385-391 (2006).
Ebden et al., "Comparison of two high dose corticosteroid aerosol treatments, beclomethasone dipropionate (500 µg/day) and budesonide (1600 µg/day), for chronic asthma," Thorax, 41:869-874, 1986.
Edwards et al., "Budesonide/formoterol for maintenance and reliever therapy of asthma: a meta analysis of randomised controlled trials," The International Journal of Clinical Practice, vol. 64(5), pp. 619-627 (2010).
Ellul-Micallef and Johansson, "Acute Dose-Response Studies in Bronchial Asthma with a New Corticosteroid, Budesonide," Br. J. Clin. Pharmac., 15:419-422, 1983.
Ellul-Micallef et al., "Budesonide: A New Corticosteroid in Bronchial Asthma," Eur J Respir Dis., 61:167-173, 1980.
Engel et al., "A trial of inhaled budesonide on airway responsiveness in smokers with chronic bronchitis," *Eur. Respir. J.* 2:935-939 (1989).
Engel et al., "Single-dose inhaled budesonide in subjects with chronic asthma," Allergy, 46:547-553, 1991.
English Translation of Opposition filed against Chilean Patent Application No. 2744-2001 (3 pages).
Fabbri et al., "Global Strategy for the Diagnosis, Management and Prevention of COPD: 2003 update," Eur. Respir. J. 22:1-2 (2003).
Fanta et al., "Glucocorticoids in Acute Asthma," American Journal of Medicine, 74:845-851, 1983.
"FDA recommends easier-to-take asthma drug" Florida Today, Associate Press, Nov. 24, 1999.
Flenley, "Chronic Obstructive Pulmonary Disease," Disease-A-Month 34:549-599 (1988).
Flenley, "Today's Treatment of Airway Obstruction . . . and Tomorrow's?," Respiration, pp. 4-9 (1989).
"Foradil" MIMS-Monthly Index of Medical Specialties Jan. 10, 1996.
"Foradil" Compendium Suisse des Medicaments, Supplement 1a pp. 7-8 (1991) (in French).
"Foradil," Compendium Suisse des Medicaments, 15th Ed. 1997/1998, Ed. Grand Public, compiled Jun. 1996, pp. 419-420, 866 (in French).
"Foradil," Compendium Suisse des Medicaments, 18th Ed. 1997, compiled Jun. 1996, pp. 849-850 and 1635 (in French).
"Foradil" Patient information leaflet, published by IKS, Switzerland (Dec. 1990) (in French).
"Foradil: Fast relief that lasts," Ciba-Geigy Limited, Switzerland, Medical and Pharmaceutical Information, 1993.
"Foradil: Fast relief that lasts," Ciba-Geigy Limited, Switzerland, Medical and Pharmaceutical Information, Update 1994 (51 pages).
Gibson et al., Respiratory Medicine Table of Contents (2002).
"GOLD: Global Initiative for Chronic Obstructive Lung Disease," Executive Summary; National Institutes of Health, National Heart Lung and Blood Institute, NIH Publication No. 2701A, pp. 1-30 (Mar. 2001).
"GOLD: Global Initiative for Chronic Obstructive Lung Disease; Global Strategy for the Diagnosis, Management, and Prevention of Chronic Obstructive Pulmonary Disease," based on Apr. 1998 NHLBI/WHO Workshop, pp. 1-100 (2004 Update).
Health Facts for You, Asthma Rescue Medicine, University of Wisconsin, Mar. 31, 2008 (2 pages).
Haughney et al., "Adjustable maintenance treatment with budesonide/formoterol combination rapidly improves and maintains quality of life in asthma patients," European Respiratory Society Annual Congress (ERS) Stockholm, Sep. 14-18, 2002, Poster Presentation, P379, submitted to EPO with letter dated Feb. 6, 2003.

Hekking et al., "Efficacy and tolerability of inhaled formoterol compared with inhaled salbutamol over three months," Symposium held during the 8th congress of the European Society of Pneumology, Freiberg, Germany, Sep. 1989.

Hett et al., "Large-Scale Synthesis of Enantic- and Diasteromerically Pure (R,R)-Formoterol," Org. Process Res. Dev., 2:96-99, 1998.

Huib et al., "A Comparison of Bronchodilator Therapy with or without Inhaled Corticosteroid Therapy for Obstructive Airways Disease," Nov. 12, 1992, The New England Journal of Medicine, vol. 327 No. 20, pp. 1413-1419.

Ind et al., "Managed Adjustable closing of budesonide/formoterol combination provides equivalent asthma control to fixed dosing at a lower overall dose," European Respiratory Society Annual Congress (ERS) Stockholm, Sep. 14-18, 2002, Poster Presentation, P2450, submitted to EPO with letter dated Feb. 6, 2003.

Jackevicius et al., "Prehospitalization Inhaled Corticosteroid Use in Patients With COPD or Asthma" Chest 111:296-302 (1997).

Jackson et al., "Benefit-Risk Assessment of Long-Acting β2-Agonists in Asthma," Drug Safety, 27(4):243-270, 2004.

Jeffery, "Structural and inflammatory changes in COPD: a comparison with asthma" Thorax 53:129-136 (1998).

Jones et al., "St George's respiratory questionnaire (SGRQ) scores may help identify COPD patients at increased risk of death over 1 year." Presentation at COPD5, Birmingham, UK, Jun. 28, 2006, Abstract 34.

Keatings et al. "Effects of Inhaled and Oral Glucocorticoids on Inflammatory Indices in Asthma and COPD" Am. J. Respir. Crit. Care Med. 155:542-548 (1997).

Kerstjens et al., "A Comparison of Bronchodilator Therapy with or without Inhaled Corticosteroid Therapy for Obstructive Airways Disease," New Eng. J. Med. 327:1413-1419 (1992).

Kesten et al., "A Three-Month Comparison of Twice Daily Inhaled Formoterol Versus Four Times Daily Inhaled Albuterol in the Management of Stable Asthma," Am Rev Respir Dis, 144:622-625, 1991.

Kumar et al., "Transient Effect of Inhaled Fluticasone on Airway Mucosal Blood Flow in Subjects with and without Asthma," Am J Respir Crit Care Med, 161:918-921, 2000.

Kuna et al., "Effect of budesonide/formoterol maintenance and reliever therapy on asthma exacerbations," International Journal of Clinical Practice, vol. 61(5), pp. 725-736 (2007), and slides based on Kuna.

Lampa et al., "Antitracheobronchospastic Interaction in Vitro and in Vivo between Salbutamol and Flunisolide," Drugs Exptl. Clin. Res., XI(9):653-658, 1985.

Leff et al., "Therapeutic Regimens in Chronic Obstructive Pulmonary Disease," Pulmon. Crit. Care Pharmacol. Therapeut. Ch. 86:837-844 (1996).

Letter from AstraZeneca to EPO dated Feb. 6, 2003 in EP Application 99930103.9.

Li, "Key Points of the new asthma guidelines," The Journal of Respiratory Diseases, 18:823-838, 1997.

Lipworth, "A Single High Dose of Budesonide Rapidly Reverses Bronchoprotective Subsensitivity and B2-Adrenocepter Down-Regulation in Patients Receiving Regular Formoterol," J. Allergy Clin. Immunol., p. S152, Section 629, Jan. 1998.

Lipworth, "Airway Subsensitivity with Long-Acting β2-Agonists," Drug Safety, vol. 16(5), pp. 295-308 (1997).

Lipworth et al., "Effects of Treatment with Formoterol on Bronchoprotection against Methacholine," Amer. J. Med., vol. 104, pp. 431-438 (1998).

Löfdahl et al., "Long-acting β2-adrenoceptor agonists: a new perspective in the treatment of asthma," The European Respiratory Journal, vol. 4, pp. 218-226 (1991).

Maesen et al., "Formoterol in the Treatment of Nocturnal Asthma" Chest 98, Oct. 4, 1990, pp. 886-870.

Maesen et al., "Bronchodilator Effect of Inhaled Formoterol vs. Salbutamol Over 12 Hours" Chest/97/3/Mar. 1990.

Marsac et al., "Inhaled beta adrenergic agonists and inhaled steroids in the treatment of asthma" Annals of Allergy Sep. 1989, vol. 63, No. 3, pp. 220-224.

Martin and Kraft, ed., Combination Therapy for Asthma and Chronic Obstructive Pulmonary Disease, Marcel Dekker, Inc., 2000, pp. 274-293.

McDonald et al., "Evaluation of the combination inhaler of salbutamol and beclomethasone dipropionate in the management of asthma," Curr. Med. Res. Opin., 11(2), 1988.

McFadden, "Inhaled Glucocorticoids and Acute Asthma: Therapeutic Breakthrough or Nonspecific Effect?" Am J Respir Crit Care Med, 157:677-678, 1998.

Minutes of the May 6, 2008 oral proceedings before the European Patent Office Technical Board of Appeal in the opposition against EP 1014993 (4 pages).

Monthly Index of Medical Specialties (MIMS), Asthma, COPD, Sep. 2007.

Monthly Index of Medical Specialties (MIMS), Bronchodilators and anti-inflammatories, Dec. 1991.

Monthly Index of Medical Specialties (MIMS), Respiratory System, Dec. 1991.

Moore et al., "Long-acting Inhaled β2-Agonists in Asthma Therapy," Chest, 113:1095-1108, 1998.

Morice et al., "A comparison of nebulized budesonide with oral prednisolone in the treatment of exacerbations of obstructive pulmonary disease," Clinical Pharmacology & Therapeutics vol. 60, pp. 675-678 (1996).

Nana et al., "High-Dose Inhaled Budesonide May Substitute for Oral Therapy After an Acute Asthma Attack," Journal of Asthma, 35:647-655, 1998.

National Asthma Education and Prevention Program, "Guidelines for the Diagnosis and Management of Asthma," Expert Panel Report Jul. 2, 1997 No. 97-4051.

New Ethicals Catalogue, Dec. 1990, No. 3 p. 50.

Niewoehner et al., "Effect of Systemic Glucocorticoids on Exacerbations of Chronic Obstructive Pulmonary Disease" New Eng. J. Med. 340(25):1941-1947 (1999).

Norman, "COPD: New Developments and Therapeutic Opportunities" Drug News Perspect. 11(7):431-437 (1998).

Notice of Opposition, filed by Ranbaxy Laboratories Limited, opposing the grant of Patent Application No. 190791 by Intellectual Property India (India Patent Office), dated Jun. 1, 2006 (21 pages).

Nyholm et al., "Therapeutic advantages of twice-daily over four-times daily inhalation budesonide in the treatment of chronic asthma," Eur J Respir Dis, 65:339-345, 1984.

O'Byrne et al., "Additive Effects of Budesonide and Formoterol in Reducing Severe Asthma Exacerbations over 12 Months," abstract of presentation given at the Jun. 1-5, 1997, Annual Meeting of Allergology and Clinical Immunology, published as abstract 266 in Allergy 52, Supp. 37-89 (1997).

O'Byrne et al., "Budesonide/Formoterol Combination Therapy as Both Maintenance and Reliever Medication in Asthma," American Journal of Respiratory and Critical Care Medicine, vol. 171, pp. 129-136 (2005).

Olsson et al., "Adjustable maintenance treatment of asthma with budesonide and formoterol in a single inhaler," European Respiratory Society Annual Congress (ERS) Stockholm, Sep. 14-18, 2002, Poster Presentation, P2451, submitted to EPO with letter dated Feb. 6, 2003.

Opponent Response in Opposition to Patent No. 19071, submitted by Lakshmi Kumaran & Sridharan, dated Nov. 3, 2006 (6 pages).

Paggiaro et al., "Multicentre randomised placebo-controlled trial of inhaled fluticasone propionate in patients with chronic obstructive pulmonary disease," The Lancet, vol. 351, pp. 773-780 (1998).

Partridge et al., "Effect on lung function and morning activities of budesonide/formoterol versus salmeterol/fluticasone in patients with COPD," Therapeutic Advances in Respiratory Disease, vol. 3(4), pp. 147-157 (2009).

Pauwels, "COPD: The Scope of the Problem in Europe" Chest 117:332S-335S (2000).

Pauwels et al., "Long-Term Treatment with Inhaled Budesonide in Persons with Mild Chronic Obstructive Pulmonary Disease Who Continue Smoking" N. Eng. J. Med. 340:1948-1953 (1999).

Pauwels et al., "Effect of Inhaled Formoterol and Budesonide on Exacerbations of Asthma," vol. 337 No. 20, Nov. 13, 1997.

Pavord et al., "Airway inflammation in patients with asthma with high-fixed or low-fixed plus as-needed budesonide/formoterol," J. Allergy Clin. Immunol., vol. 123(5), pp. 1083-1089.e7 (2009).

Pearson et al., "British Thoracic Society Guidelines for Treatment of COPD" Thorax 52 (Suppl. 5):S1-S28 (1997).

Poitiek et al., "Comparison of formoterol, salbutamol and salmeterol in methacholine-induced severe bronchoconstriction β2-Agonists in Methacholine-Induced Bronchoconstriction", Eur Respir J., 13:988-992, 1999.

Product Information for "Foradil Dosis-aerosol," Netherlands authorization date Mar. 4, 1992, Medicines Data Bank (downloaded from the Internet on Jan. 28, 2005), followed by a nine-page printout from the register of the Medicines Evaluation Board of the Netherlands regarding formoterol fumerate dihydrate, dated Jul. 15, 2003, pp. 1-9.

Postma, "Inhaled therapy in COPD: what are the benefits?" Respiratory Medicine 85:447-449 (1991).

Postma et al., "Rationale for the Dutch Hypothesis* Allergy and Airway Hyperresponsiveness as Genetic Factors and Their Interaction With Environment in the Development of Asthma and COPD" Chest 126:96S-104S (2004).

"Pulmicort" ABPI Data Sheet Compendium, p. 146-147 (1995/1996).

Price et al., "Budesonide/formoterol with an adjustable maintenance plan costs less and is as effective as fixed dosing," European Respiratory Society Annual Congress (ERS) Stockholm, Sep. 14-18, 2002, Poster Presentation, P2452, submitted to EPO with letter dated Feb. 6, 2003.

Rabe, "Combination therapy for chronic obstructive pulmonary disease; one size fits all?" Eur. Respir. J. 22:874-875 (2003).

Rabe et al., "Budesonide/Formoterol in a Single Inhaler for Maintenance and Relief in Mild-to Moderate Asthma," Chest, 129:246-256, 2006.

Rabe et al., "The challenge of long-acting β-adrenoceptor agonists," Respiratory Medicine, vol. 85, pp. 5-9 (1991).

Rabe et al., "Effect of budesonide in combination with formoterol for reliever therapy in asthma exacerbations: a randomized controlled, double-blind study," The Lancet, vol. 368, pp. 744-753 (2006) and slides based on Rabe et al.

Rees, "β2 Agonists and asthma," BMJ, 302:1166-1167, 1991.

Renkema et al., CA 126:259329.

Renkema et al., "Effects of Long-term Treatment With Corticosteroids in COPD" Chest 109:1156-1162 (1996).

Rennard et al., "Efficacy and Tolerability of Budesonide/Formoterol in One Hydrofluoroalkane Pressurized Metered-Dose Inhaler in Patients with Chronic Obstructive Pulmonary Disease," Drugs, vol. 69(5), pp. 549-565 (2009).

Reply statement before the Opposition Board, Patent Office, Delhi; submitted on behalf of AstraZeneca, dated Jul. 27, 2006 (6 pages).

Response by Astra to EPO, dated Nov. 22, 1995.

Response to EPO Office Action in opposition against EP 108577, sent by AstraZeneca, dated Oct. 5, 2009 (17 pages).

Response to an Opposition in Chilean Application No. 2744/2001, dated Aug. 6, 2006, English Translation included (6 pages).

Request for Revocation of the Corresponding Patent in Turkey (TR 2000 00726), dated Jun. 6, 2009 (15 pages).

Roberts et al., "Which patients are prescribed inhaled anti-asthma drugs?" Thorax 49(11):1090-1095 (1994).

Rodrigo et al., "Inhaled Flunisolide for Acute Severe Asthma," Am J Respir Crit Care Med, 157:698-703, 1998.

Rodrigo et al., "Acute Asthma in Adults: A Review," Chest, 125:1081-1102, 2004.

Rosenborg et al., "Relative systemic dose potency and tolerability of inhaled formoterol and salbutamol in healthy subjects and asthmatics," Eur J. Clin Pharmacol., 56:363-370, 2000.

Rosenhall et al., "Efficacy, safety and cost of budesonide/formoterol in a single inhaler compared with budeonside plus formoterol as separate inhalers", European Respiratory Society Annual Congress (ERS) Stockholm, Sep. 14-18, 2002, Poster Presentation, P388, submitted to EPO with letter dated Feb. 6, 2003.

Ryrfeldt et al., "Pulmonary disposition of the potent glucocorticoid budesonide evaluated in an isolated perfused rat lung model," Biochem Pharmacol., 38:17-22, 1989.

Schuh et al., "A Comparison of Inhaled Fluticasone and Oral Prednisone for Children with Severe Acute Asthma," New England Journal of Medicine, 343:689-694, 2000.

Schultze-Werninghaus, "Multicenter 1-Year Trial on Formoterol, a New Long-Acting β2-Agonist, in Chronic Obstructive Airway Disease," Lung Suppl:83-89 (1990).

Scicchitano et al., "Efficacy and safety of budesonide/formoterol single inhaler therapy versus a higher dose of budesonide in moderate to severe asthma," Current Medical Research and Opinion, vol. 20(9), pp. 1403-1418 (2004).

Scrip, The Dialog Corporation, 1562, p. 21 (Oct. 31, 1990).

Sears et al., "Regular inhaled beta-agonist treatment in bronchial asthma," Lancet, 336:1391-1396, 1990.

Shepherd et al., "Regular Versus Symptomatic Aerosol Bronchodilator Treatment of Asthma," Br. J. Dis. Chest, vol. 75, pp. 215-217 (1981).

Siafakas et al., "Optimal Assessment and Management of Chronic Obstructive Pulmonary Disease (COPD)," Eur. Respir. J. 8:1398-1420 (1995).

Smeenk et al., "Opportunistische longinfecties bij patienten met chronische obstructieve longziekte; een bijwerking van inhalatiecorticosteroiden?" Nederlands Tijdschrift voor Geneeskunde, 140(2):94-98, 1996, Partial English translation dated Mar. 11, 2003, included.

Smeenk et al., "Opportunistic Lung Infections in Patients with Chronic Obstructive Pulmonary Disease—A Side Effect of Inhalation Corticosteroids?" Nederlands Tijdschrift Geneeskunde, vol. 13, Jan. Issue 140(2) 1996, pp. 94-98. (Full English translation).

Soriano et al., "Inhaled Corticosteroids with/Without Long-Acting βAgonists Reduce the Risk of Rehospitalization and Death in COPD Patients," Am. J. Respir. Medic. 2:67-74 (2003).

Soriano et al., "The Proportional Venn Diagram of Obstructive Lung Disease* Two Approximations From the United States and the United Kingdom" Chest 124:474-481 (2003).

Stalenheim et al., "Efficacy and Tolerance of a 12-Week Treatment with Inhaled Formoterol in Patients with Reversible Obstructive Lung Disease," Respiration 61:305-309 (1994).

Statement of Grounds of Opposition to patent EP1085877 by Vectura Limited, received at the EPO on Dec. 17, 2008.

Statement of Grounds of Opposition to patent EP1085877 by Generics Limited, received at the EPO on Dec. 19, 2008.

Statement of Grounds of Opposition to patent EP1085877 by Norton Health Care Limited, received at the EPO on Dec. 19, 2008.

Statement of Grounds of Opposition to patent EP1085877 by Ratiopharm GmbH, received at the EPO on Dec. 17, 2008, translation attached.

Sue et al., "A Comparison of Intravenous Hydrocortisone, Methylprednisolone, and Dexamethasone in Acute Bronchial Asthma," Annals of Allergy, 56:406-409, 1986.

Sung et al., "Randomized, Controlled Trial of Inhaled Budesonide as an Adjunct to Oral Prednisone in Acute Asthma," Academic Emergency Medicine, vol. 5(3), pp. 209-212 (1998).

Sykes et al., "A study of the duration of the bronchodilator effect of 12 ug and 24 ug of inhaled formoterol and 200 ug inhaled salbutamol in asthma," Respir. Med., 84:135-138, 1990.

Szafranski et al., "Efficacy and safety of budesonide/formoterol in the management of chronic obstructive pulmonary disease" Eur. Respir. J. 21:74-81 (2003).

Tan et al., "Systemic Corticosteroid Rapidly Reverses Bronchodilator Subsensitivity induced by Formoterol in Asthmatic Patient," Am. J. Respiratory and Critical Care Medicine, 156:28-35, 1997.

Tashkin et al., "Efficacy and Safety of Budesonide and Formoterol in One Pressurized Metered-Dose Inhaler in Patients with Moderate to Very Severe Chronic Obstructive Pulmonary Disease," Drugs, vol. 68(14); pp. 1975-2000 (2008).

Tattersfield et al. on behalf of the Facet International Study Group, "Exacerbations of Asthma," Am J Respir Crit Care Med, 160:594-599, 1999.

Taylor et al., "A new perspective on concepts of asthma severity and control," Eur. Respir. J. vol. 32, pp. 545-554 (2008).

The Dialog Corporation, "Formoterol launched in Switzerland," Accession No: S002557609000, Oct. 31, 1990.

The Merck Manual of Diagnosis and Therapy, 16th edition, 1992, p. 653.

The Patents Act 1953 Exhibit "CRWB1."
The Patents Act 1953 Exhibit "CRWB3."
The Patents Act 1953 Exhibit "CRWB4."
The Patents Act 1953 Exhibit "CRWB5."
The Patents Act 1953 Exhibit "CRWB6."

Trechsel, "Foradil in medical practice: 7 case studies" Ciba-Geigy Limited, Switzerland (1992).
Tierney, et al., Disorders of the Airways, Current Medical Diagnosis and Treatment, Chapter 9, pp. 241-255, (1997).
Urbano, "Review of the NAEPP 2007 Expert Panel Report (EPR-3) on Asthma Diagnosis and Treatment Guidelines," Journal of Managed Care Pharmacy, vol. 14(1), pp. 41-49 (2008).
U.S. Department of Health and Human Services, "Practical Guide for the Diagnosis and Management of Asthma," Oct. 1997 NIH Publication No. 97-4053.
Van Schayck et al., "Do patients with COPD benefit from treatment with inhaled corticosteroids?" Eur. Respir. J. 9:1969-1972 (1996).
Vanzieleghem et al., "A comparison of budesonide and beclomethasone dipropionate nasal aerosols in ragweed-induced rhinitis," J. Allergy Clin. Immunology, 79:887-892, 1987.
Van Andel et al., "Analysis of Inhaled Corticosteroid and Oral Theophylline Use Among Patients With Stable COPD from 1987 to 1995" Chest 115:703-707 (1999).
Venner Shipley LLP, Letter to the European Patent Office regarding opposition to EP Patent No. 1085877, filed by Generics (UK) Limited (Apr. 20, 2010).
Vestbo et al., "Update on the "Dutch hypothesis" for chronic respiratory disease" Thorax 53(Suppl.2):S15-S19 (1998).
Vestbo et al., "Long-term effect of inhaled budesonide in mild and moderate chronic obstructive pulmonary disease: a randomised controlled trial," Lancet 353:1819-1823 (1999).
Waalkens et al., "Budesonide and terbutaline or terbutaline alone in children with mild asthma: effects on bronchial hyperresponsiveness and diurnal variation in peak flow," Thorax, 46:499-503, 1991.
Wallin et al., "Formoterol, a new long acting beta2 agonist for inhalation twice daily, compared with salbutamol in the treatment of asthma," Thorax, 45:259-261, 1990.
Wasserman, "What Is a Rescue Medicine and When Is It Used to Treat Asthma?" ABC News, 2 pages. (2008).
Watson et al. "Failure of Inhaled Corticosteroids to Modify Bronchoconstrictor or Bronchodilator Responsiveness in Middle-Aged Smokers with Mild Airflow Obstruction" Chest 101:350-355 (1992).
Weiner et al., "Inhaled Budesonide Therapy for Patients with Stable COPD," Chest 108:1568-1571 (1995).
Welte et al., "Efficacy and Tolerability of Budesonide/Formoterol Added to Tiotropium in Patients with Chronic Obstructive Pulmonary Disease," Am. J. Respir. Crit. Care Med., vol. 180, pp. 741-750 (2009).
Wempe et al., "Effects of corticosteroids on bronchodilator action in chronic obstructive lung disease", Thorax, vol. 47, pp. 616-621 (1992).
Wilcke et al., "The effect of inhaled glucocorticosteroids in emphysema due to α1-antitrypsin deficiency," Respiratory Medicine, vol. 91, pp. 275-279 (1997).
"What You Should Know About Symbicort Turbohaler?" AstraZeneca, May 2001, 4 pages.
Written decision of the European Patent Office Technical Board of Appeal in the opposition against EP 1014993, dated May 6, 2008 (17 pages).
Wyser et al., "Neu Aspekte in der Behandlung des Asthma bronchiale und chronisch obstruktiver Lungenkrankheiten, Schweiz-Med Wochenschr," vol. 127, pp. 885-890 (1997), English Summary included.
USPTO Office Action in U.S. Appl. No. 09/194,290, mailed Aug. 16, 1999 (Rescinded) (5 pages).
USPTO Office Action in U.S. Appl. No. 09/194,290, mailed Mar. 27, 2000 (case abandoned Oct. 2, 2000) (6 pages).
USPTO Office Action in U.S. Appl. No. 09/670,457, mailed May 10, 2001 (case abandoned Nov. 30, 2001) (6 pages).
USPTO Office Action in U.S. Appl. No. 09/367,950, mailed Dec. 18, 2000 (9 pages).
Fish & Richardson P.C., Amendment in Reply to Office Action dated Dec. 18, 2001, in U.S. Appl. No. 09/367,950, filed Apr. 18, 2001 (8 pages).
USPTO Final Office Action in U.S. Appl. No. 09/367,950, mailed May 21, 2001 (8 pages).
Fish & Richardson P.C., Response to Final Office Action dated May 21, 2001, in U.S. Appl. No. 09/367,950, filed Aug. 21, 2001 (4 pages).
USPTO Office Action in U.S. Appl. No. 09/367,950, mailed Sep. 25, 2001 (8 pages).
Fish & Richardson P.C., Response to Office Action dated May 21, 2001, in U.S. Appl. No. 09/367,950, filed Dec. 26, 2001 (3 pages).
USPTO Final Office Action in U.S. Appl. No. 09/367,950, mailed Apr. 15, 2002 (6 pages).
In U.S. Appl. No. 09/369,950, Interview Summary dated Sep. 17, 2002 (1 page).
Fish & Richardson P.C., Notice of Appeal in U.S. Appl. No. 09/367,950, filed Oct. 9, 2002 (1 page).
Fish & Richardson P.C., Request for Continued Examination and Amendment in Reply in U.S. Appl. No. 09/367,950, filed Dec. 10, 2002 (55 pages).
USPTO Office Action in U.S. Appl. No. 09/367,950, mailed Mar. 21, 2003 (9 pages).
Fish & Richardson P.C., Response to Office Action dated Mar. 21, 2003, in U.S. Appl. No. 09/367,950, filed Jun. 19, 2003 (9 pages).
Fish & Richardson P.C., Supplemental Amendment filed Jul. 3, 2003, in U.S. Appl. No. 09/367,950 (8 pages).
Notice of Allowance mailed Jul. 9, 2003, in U.S. Appl. No. 09/367,950 (9 pages).
USPTO Office Action in U.S. Appl. No. 09/367,950, mailed May 4, 2004 (12 pages).
Fish & Richardson P.C., Reply to Office Action dated May 4, 2004, in U.S. Appl. No. 09/367,950 filed Nov. 1, 2004 (6 pages).
USPTO Office Action in U.S. Appl. No. 09/367,950, mailed Mar. 30, 2005 (14 pages).
Fish & Richardson P.C., Amendment in Reply to Office Action dated Mar. 30, 2005, in U.S. Appl. No. 09/367,950, filed Jun. 29, 2005 (17 pages).
USPTO Office Action in U.S. Appl. No. 09/367,950, mailed Sep. 21, 2005 (15 pages).
Fish & Richardson P.C., Amendment in Reply to Office Action dated Sep. 21, 2005, in U.S. Appl. No. 09/367,950, filed Nov. 15, 2005 (12 pages).
Advisory Action in U.S. Appl. No. 09/367,950, mailed Dec. 14, 2005 (3 pages).
Fish & Richardson P.C., Brief on Appeal filed Mar. 3, 2006, in U.S. Appl. No. 09/367,950, filed Mar. 3, 2006 (61 pages).
Examiner's Answer in U.S. Appl. No. 09/367,950, mailed Jun. 16, 2006 (15 pages).
Fish & Richardson P.C., Reply Brief on Appeal filed Aug. 14, 2006, in U.S. Appl. No. 09/367,950 (15 pages).
Communication regarding Appeal Brief in U.S. Appl. No. 09/367,950, mailed Sep. 12, 2006 (2 pages).
Notice of Non-Compliant Appeal Brief in U.S. Appl. No. 09/367,950, mailed Oct. 30, 2006 (4 pages).
Fish & Richardson P.C., Amendment in Reply to Notice of Non-Compliant Appeal Brief dated Oct. 30, 2006, in U.S. Appl. No. 09/367,950 filed Nov. 28, 2006 (8 pages).
Office Communication dated Jan. 24, 2007, in U.S. Appl. No. 09/367,950 (2 pages).
Board of Appeals and Interferences, Order remanding to the Examiner, in U.S. Appl. No. 09/367,950, dated Aug. 28, 2007 (11 pages).
Interview Summary mailed Oct. 22, 2007, in U.S. Appl. No. 09/367,950 (4 pages).
Fish & Richardson P.C., Interview Summary Following Board Decision of Aug. 28, 2007, dated Nov. 9, 2007 and re-filed Nov. 21, 2007 in U.S. Appl. No. 09/367,950 (13 pages).
Office Action in U.S. Appl. No. 09/367,950, mailed Dec. 4, 2007 (16 pages).
Fish & Richardson P.C., Amendment in Reply to Office Action dated Dec. 4, 2007, in U.S. Appl. No. 09/367,950 filed Jun. 3, 2008 (37 pages).
Final Office Action in U.S. Appl. No. 09/367,950, mailed Oct. 6, 2008 (21 pages).
Fish & Richardson P.C., Amendment in Reply to Final Office Action dated Oct. 6, 2008, in U.S. Appl. No. 09/367,950 filed Apr. 3, 2009 (20 pages).
Office Action in U.S. Appl. No. 10/665,240, mailed Jan. 30, 2007 (18 pages).

Fish & Richardson P.C., Amendment in Reply to Final Office Action dated Jan. 30, 2007, in U.S. Appl. No. 10/665,240, filed Jul. 27, 2007 (30 pages).
Final Office Action in U.S. Appl. No. 10/665,240, mailed Oct. 18, 2007 (25 pages).
Fish & Richardson P.C., Amendment in Reply to Final Office Action dated Oct. 18, 2007, in U.S. Appl. No. 10/665,240, filed Apr. 17, 2008 (14 pages).
Advisory Action Before the Filing of an Appeal Brief, in U.S. Appl. No. 10/665,240, dated May 5, 2008 (5 pages).
Final Office Action in U.S. Appl. No. 10/665,240, mailed Sep. 19, 2008 (16 pages).
Fish & Richardson P.C., Amendment in Reply to Final Office Action dated Sep. 19, 2008, in U.S. Appl. No. 10/665,240, filed Mar. 18, 2009 (21 pages).
Final Office Action in U.S. Appl. No. 10/665,240, mailed Jun. 12, 2009 (25 pages).
Office Action from U.S. Appl. No. 09/367,950, mailed Jun. 25, 2009 (21 pages).
Fish & Richardson P.C., Reply to Office Action in U.S. Appl. No. 10/665,240, filed Dec. 11, 2009 (12 pages).
Fish & Richardson P.C., Reply to Office Action in U.S. Appl. No. 09/367,950, filed Dec. 21, 2009 (14 pages).
Office Action in U.S. Appl. No. 10/665,240, mailed Mar. 4, 2010 (27 pages).
Final Office Action in U.S. Appl. No. 09/367,950, mailed Mar. 17, 2010 (19 pages).
Fish & Richardson Response to Office Action in U.S. Appl. No. 10/665,240, mailed Mar. 4, 2010, filed Jun. 3, 2010 (24 pages).
EPO Office Action from EP Serial No. 03 002 381.6-2123, dated Jun. 7, 2010 (5 pages).
Fish & Richardson P.C., Response to Final Office Action, in U.S. Appl. No. 09/367,950, filed Jun. 16, 2010 (22 pages).
Final Office Action in U.S. Appl. No. 10/665,240, mailed Aug. 20, 2010 (26 pages).
Din Link Prescribing data: Steroids and long acting bronchodilators, Aug. 1992-Aug. 1997, submitted on Sep. 17, 2004, by Norton Healthcare in an European Patent Office opposition against EP 1014993 B1.
Product insert for Advair Diskus®, Patient's Instructions for Use (3 pages), 2003.
Product insert for Symbicort® Turbuhaler® (2 pages) (2001).
Product insert for Pulmicort Turbuhaler® (4 pages), Jun. 1997.
Statutory Declaration of Charles Richard William Beasley, Curriculum Vitae of Charles Richard William Beasley (1998).
Stedman's Medical Dictionary, 25th ed., Baltimore: Williams and Wilkins; p. 428, Feb. 20, 1995.
Treschel, AM Conference Report, A new long-active beta-stimulator, Apr. 12, 1991.
"Ventide Inhaler," ABPI Data Sheet Compendium (3 pages), Jan. 24, 1991.
Observations from Elkington and Fife LLP dated Sep. 17, 2004 in European opposition (12 pages).
Submission dated Sep. 29, 2011 by opponent in opposition on European Patent No. 1 085 877.
The 1993 British Thoracic Society Guidelines for the Management of Asthma, as published in Thorax, vol. 48, supplement S1-S24, 1993.
G. Schültz-Werninghaus, "Long-term treatment with inhaled formoterol over one year", 8th Congress of the European Society of Pneumology, pp. 46-50, Sep. 1989, published 1990.
B. Lundback et al., "Twelve month comparison of salmeterol and salbutamol as dry powder formulations in asthmatic patients", Thorax, vol. 48, pp. 148-153, 1993.
Ed. P.J. Barnes et al., Asthma, Lippincott-Ravan, USA, Chapter 126, vol. 2, pp. 1854-1857, 1997.
Statement of Professor Neil Christopher Barnes, dated Jul. 26, 2011, 5 pages.
Second Statement of Professor Neil Christopher Barnes, dated Sep. 8, 2011, 4 pages.
S. Kesten, et al., "Sustained improvement in asthma with long-term use of formoterol fumarate," Annals of Allergy, vol. 69, pp. 415-420 (1992).
Fish & Richardson P.C., Brief on Appeal in U.S. Appl. No. 10/665,240, filed Aug. 2, 2011, 67 pages.
Examiner's Answer in U.S. Appl. No. 10/665,240, mailed Oct. 27, 2011, 22 pages.
Fish & Richardson P.C., Reply Brief in U.S. Appl. No. 10/665,240, filed Dec. 27, 2011, 62 pages.
Letter from Kim & Chang regarding Korean Patent Court's written opinion regarding Korean patent, dated May 29, 2008, 11 pages.

* cited by examiner

USE FOR BUDESONIDE AND FORMOTEROL

This application is a continuation of U.S. application Ser. No. 10/010,283, filed Nov. 13, 2001, which is a continuation of U.S. application Ser. No. 09/670,457, filed Sep. 26, 2000 (now abandoned), which is a continuation of U.S. application Ser. No. 09/194,290, filed Nov. 23, 1998 (now abandoned), which is a 35 U.S.C. §371 national phase application of International application no. PCT/SE98/01599, filed Sep. 9, 1998, which claims priority to Swedish Patent Application No. 9703407-8, filed Sep. 19, 1997. The disclosures of the prior applications are considered part of (and are incorporated by reference in) the disclosure of this application.

FIELD OF THE INVENTION

The invention provides the use of formoterol and budesonide in the treatment of chronic obstructive pulmonary disease (COPD).

BACKGROUND TO THE INVENTION

Chronic obstructive pulmonary disease (COPD) is a term which refers to a large group of lung diseases which can interfere with normal breathing. It is estimated that 11% of the U.S. population has COPD and the incidence is increasing. The two most important conditions covered by COPD are chronic bronchitis and emphysema.

Chronic bronchitis is a long-standing inflammation of the bronchi which causes increased production of mucous and other changes. The patients' symptoms are cough and expectoration of sputum. Chronic bronchitis can lead to more frequent and severe respiratory infections, narrowing and plugging of the bronchi, difficult breathing and disability.

Emphysema is a chronic lung disease which affects the alveoli and/or the ends of the smallest bronchi. The lung loses its elasticity and therefore these areas of the lungs become enlarged. These enlarged areas trap stale air and do not effectively exchange it with fresh air. This results in difficult breathing and may result in insufficient oxygen being delivered to the blood. The predominant symptom in patients with emphysema is shortness of breath.

At present moderate to severe COPD is treated with a variety of monotherapies including inhaled or orally administered bronchodilators, inhaled anti-cholinergic agents and orally administered steroids, especially corticosteroids. The problem with these treatments is that none of them is especially effective. For example, many patients with COPD have a reversible component. Accordingly a new treatment is required for decreasing the intensity of exacerbations, thereby improving the lung function of patients suffering from COPD.

DESCRIPTION OF THE INVENTION

It has surprisingly been found that the combination of formoterol and budesonide is effective in treating COPD.

The combination of budesonide and formoterol reduces the number of exacerbations of COPD compared to the monotherapies using budesonide or formoterol, thereby improving the lung function of the patients. Thus, the combination of budesonide and formoterol will give greater compliance, greater efficacy, less exacerbations and/or better sleep.

The present invention also gives an increased compliance and efficacy and thereby quality of life.

According to the invention there is provided the use of a composition comprising, in admixture or separately:

(a) a first active ingredient which is formoterol, a pharmaceutically acceptable salt or solvate thereof, or a solvate of such a salt;
(b) a second active ingredient which is budesonide; and
a molar ratio of the first active ingredient to the second active ingredient of from 1:2500 to 12:1,
in the manufacture of a medicament for use in the treatment of chronic obstructive pulmonary disease.

The composition used in the invention optionally additionally comprises one or more pharmaceutically acceptable additives, diluents and/or carriers. The composition is preferably in the form of a dry powder, wherein the particles of the pharmaceutically active ingredients preferably have a mass median diameter of less than 10 µm.

The invention also includes the use of a kit containing:
 (i) a vessel containing the first active ingredient;
 (ii) a vessel containing the second active ingredient;
 (iii) a molar ratio of the first active ingredient to the second active ingredient of from 1:2500 to 12:1; and
 (iv) instructions for the simultaneous, sequential or separate administration of the active ingredients to a patient in need thereof;
in the manufacture of a medicament for use in the treatment of chronic obstructive pulmonary disease.

A patient suffering from COPD can be treated by administering via inhalation a composition as defined above. Alternatively such a patient can be treated by administering via inhalation, simultaneously, sequentially or separately, (i) a dose of the first active ingredient; and (ii) a dose of the second active ingredient. The molar ratio of the first active ingredient to the second active ingredient is from 1:2500 to 12. The doses can be provided to the patient for inhalation in dry powder form.

The invention further provides the use of budesonide and of formoterol in the manufacture of a composition or a kit, as used in the invention, for use in the treatment of chronic obstructive pulmonary disease.

The first and second active ingredients of the kit used in the invention can be administered simultaneously, sequentially or separately to COPD. By sequential is meant that the first and second active ingredients are administered one after the other. They still have the desired effect if they are administered separately but less than about 12 hours apart, preferably less than about 2 hours apart, more preferably less than about 30 minutes apart, and most preferably one immediately after the other.

The molar ratio of the first active ingredient to the second active ingredient is suitably from 1:555 to 2:1 and preferably from 1:150 to 1:1. The molar ratio of the first active ingredient to the second active ingredient is more preferably from 1:133 to 1:6. The molar ratio of the first active ingredient to the second active ingredient can also be 1:70 to 1:4.

Preferably the amount of the first active ingredient used is preferably from 2 to 120 nmol (more preferably from 7 to 70 nmol). The amount of the second active ingredient used is preferably from 0.1 to 5 µmol (preferably 0.15 to 4 µmol) or from 45 to 2200 µg, more preferably from 65 to 1700 µg.

Throughout the specification, the amount of the first and second active ingredient used relate to unit doses unless explicitly defined differently.

Suitable physiologically acceptable salts of formoterol include acid addition salts derived from inorganic and organic acids, for example the chloride, bromide, sulphate, phosphate, maleate, fumarate, tartrate, citrate, benzoate, 4-methoxybenzoate, 2- or 4-hydroxybenzoate, 4-chlorobenzoate, p-toluenesulphonate, methanesulphonate, ascorbate, acetate, succinate, lactate, glutarate, gluconate, tricarballylate, hydroxynaphthalene-carboxylate or oleate salts or solvates thereof. The first active ingredient is preferably formoterol fumarate, especially the dihydrate thereof.

When the first active ingredient is formoterol fumarate dihydrate, the amount of the first active ingredient used is suitably from 1 to 50 µg, more suitably from 3 to 30 µg.

Preferably the composition or kit used in the invention comprises unit doses of 6 µg of formoterol fumarate dihydrate and 100 µg of budesonide, or 4.5 µg of formoterol fumarate dihydrate and 80 µg of budesonide, either of which is administered up to four times a day. Alternatively the composition or kit of the invention comprises unit doses of 12 µg of formoterol fumarate dihydrate and 200 µg of budesonide, or 9 µg of formoterol fumarate dihydrate and 160 µg of budesonide, either of which is administered once or twice a day.

More preferably the composition or kit used in the invention comprises unit doses of 6 µg of formoterol fumarate dihydrate and 200 µg of budesonide, or 4.5 µg of formoterol fumarate dihydrate and 160 µg of budesonide, either of which is administered up to four times a day. Alternatively the composition or kit of the invention comprises unit doses of 12 µg of formoterol fumarate dihydrate and 400 µg of budesonide, or 9 µg of formoterol fumarate dihydrate and 320 µg of budesonide, either of which is administered once or twice a day.

Most preferably the composition or kit used in the invention comprises unit doses of 6 µg of formoterol fumarate dihydrate and 400 µg of budesonide, or 4.5 µg of formoterol fumarate dihydrate and 320 µg of budesonide, either of which is administered up to four times a day.

Preferably the active ingredient(s) are used in admixture with one or more pharmaceutically acceptable additives, diluents or carriers, preferably in an amount of from 50 µg to 25 mg per dose, more preferably in an amount of from 50 µg to 10 mg, most preferably in an amount of from 100 to 2000 µg per unit dose. Examples of suitable diluents or carriers include lactose, dextran, mannitol or glucose. Preferably lactose is used, especially as the monohydrate.

One or more of the ingredients is preferably in the form of a dry powder, more preferably a finely divided powder, e.g. micronised dry powder, most preferably an agglomerated micronised dry powder. As an alternative to agglomeration, the finely divided active ingredients may be in the form of an ordered mixture with the pharmaceutically acceptable additive, diluent or carrier. An ordered mixture comprises fine particles of an active ingredient in association with coarse particles or a mixture of coarse and finely divided particles of the pharmaceutically acceptable additive, diluent or carrier. The ingredients used in the invention can be obtained in these preferred forms using methods known to those of skill in the art. The particle size of the active ingredients is preferably less than 10 µm.

Administration may be by inhalation orally or intranasally. The active ingredients are preferably adapted to be administered, either together or individually, from dry powder inhaler(s) (DPIs), especially Turbuhaler® (Astra AB), pressurised metered dose inhaler(s) (pMDIs), or nebuliser(s).

When the active ingredients are adapted to be administered, either together or individually, from pressurised inhaler(s), they are preferably in finely divided, and more preferably in micronised form. They may be dissolved or, preferably, suspended in a liquid propellant mixture. The propellants which can be used include chlorofluorocarbons, hydrocarbons or hydrofluoroalkanes. Especially preferred propellants are P134a (tetrafluoroethane) and P227 (heptafluoropropane) each of which may be used alone or in combination. They are optionally used in combination with one or more other propellants and/or one or more surfactants and/or one or more other excipients, for example ethanol, a lubricant, an anti-oxidant and/or a stabilising agent.

When the active ingredients are adapted to be administered, either together or individually, via nebuliser(s) they may be in the form of a nebulised aqueous suspension or solution, with or without a suitable pH or tonicity adjustment, either as a unit dose or multidose device.

The composition or kit used in the invention may optionally be administered as divided doses from 1 to 4, and preferably once or twice a day.

The invention is illustrated by the following Examples which are not intended to limit the scope of the application. In the Examples micronisation is carried out in a conventional manner such that the particle size range for each component is suitable for administration by inhalation. Turbuhaler® is a trademark of Astra AB.

EXAMPLE 1

6 Parts by weight of formoterol fumarate dihydrate was mixed with 794 parts by weight of lactose monohydrate. The blend was micronised using a high pressure air jet mill and then conditioned using the process of EP-A-717 616. 200 Parts by weight of micronised budesonide was added to the conditioned product by mixing and homogenising with a low pressure jet mill. The mixture was then spheronised using the process of EP-A-721 331 and filled into the storage compartment of a Turbuhaler® dry powder inhaler.

EXAMPLE 2

4.5 Parts by weight of formoterol fumarate dihydrate was mixed with 835 parts by weight of lactose monohydrate. The blend was micronised using a high pressure air jet mill and then conditioned using the process of EP-A-717 616. 160 Parts by weight of micronised budesonide was added to the conditioned product by mixing and homogenising with a low pressure jet mill. The mixture was then spheronised using the process of EP-A-721 331 and filled into the storage compartment of a Turbuhaler® dry powder inhaler.

EXAMPLE 3

12 Parts by weight of formoterol fumarate dihydrate was mixed with 588 parts by weight of lactose monohydrate. The blend was micronised using a high pressure air jet mill and then conditioned using the process of EP-A-717 616. 400 Parts by weight of micronised budesonide was added to the conditioned product by mixing and homogenising with a low pressure jet mill. The mixture was then spheronised using the process of EP-A-721 331 and filled into the storage compartment of a Turbuhaler® dry powder inhaler.

EXAMPLE 4

6 Parts by weight of formoterol fumarate dihydrate was mixed with 894 parts by weight of lactose monohydrate. The blend was micronised using a high pressure air jet mill and then conditioned using the process of EP-A-717 616. 100 Parts by weight of micronised budesonide was added to the conditioned product by mixing and homogenising with a low pressure jet mill. The mixture was then spheronised using the process of EP-A-721 331 and filled into the storage compartment of a Turbuhaler® dry powder inhaler.

EXAMPLE 5

4.5 Parts by weight of formoterol fumarate dihydrate was mixed with 915 parts by weight of lactose monohydrate. The blend was micronised using a high pressure air jet mill and then conditioned using the process of EP-A-717 616. 80 Parts by weight of micronised budesonide was added to the conditioned product by mixing and homogenising with a low pressure jet mill. The mixture was then spheronised using the process of EP-A-721 331 and filled into the storage compartment of a Turbuhaler® dry powder inhaler.

EXAMPLE 6

12 Parts by weight of formoterol fumarate dihydrate was mixed with 788 parts by weight of lactose monohydrate. The blend was micronised using a high pressure air jet mill and then conditioned using the process of EP-A-717 616. 200 Parts by weight of micronised budesonide was added to the conditioned product by mixing and homogenising with a low pressure jet mill. The mixture was then spheronised using the process of EP-A-721 331 and filled into the storage compartment of a Turbuhaler® dry powder inhaler.

EXAMPLE 7

6 Parts by weight of formoterol fumarate dihydrate was mixed with 994 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

200 Parts by weight of micronised budesonide was mixed with 800 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

EXAMPLE 8

4.5 Parts by weight of formoterol fumarate dihydrate was mixed with 995 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

160 Parts by weight of micronised budesonide was mixed with 840 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

EXAMPLE 9

12 Parts by weight of formoterol fumarate dihydrate was mixed with 988 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

400 Parts by weight of micronised budesonide was mixed with 600 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

EXAMPLE 10

6 Parts by weight of formoterol fumarate dihydrate was mixed with 994 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

100 Parts by weight of micronised budesonide was mixed with 900 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

EXAMPLE 11

4.5 Parts by weight of formoterol fumarate dihydrate was mixed with 995 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

80 Parts by weight of micronised budesonide was mixed with 920 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

EXAMPLE 12

12 Parts by weight of formoterol fumarate dihydrate was mixed with 988 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

200 Parts by weight of micronised budesonide was mixed with 800 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

EXAMPLE A

Patients suffering from COPD are first put through a run-in period of 2 weeks and are then split into 4 groups of approximately equal numbers. Each group is then given either budesonide/formoterol, budesonide alone, formoterol alone or placebo for a period of 12 months.

The following parameters for each patient are monitored throughout: mild and severe exacerbations, $FEV_1$ (forced expiratory volume in one second), vital capacity (VC), peak expiratory flow (PEF), symptom scores and Quality of Life. Of these, mild and severe exacerbations are considered to be primary efficacy variables, whereas the remaining parameters are considered to be secondary efficacy variables.

The invention claimed is:

1. A method for treating a patient suffering from chronic obstructive pulmonary disease (COPD), the method comprising administering to the patient via inhalation a composition comprising formoterol fumarate dihydrate and budesonide.

2. The method of claim 1, wherein the composition is administered to the patient in unit doses, each unit dose delivering to the patient 1 to 50 µg formoterol fumarate dihydrate and 45 to 2200 µg budesonide.

3. The method of claim 1, wherein the composition is administered to the patient in unit doses, each unit dose delivering to the patient 3 to 30 µg formoterol fumarate dihydrate and 45 to 2200 µg budesonide.

4. The method of claim 1, wherein the composition is administered to the patient in unit doses, each unit dose delivering to the patient 4.5 or 9 µg formoterol fumarate dihydrate.

5. The method of claim 1, wherein the composition is administered to the patient in unit doses, each unit dose delivering to the patient 80, 160, or 320 µg budesonide.

6. The method of claim 1, wherein the composition is administered to the patient in unit doses, each unit dose delivering to the patient 4.5 µg formoterol fumarate dihydrate and 80 or 160 µg budesonide.

7. The method of claim 1, wherein the composition is administered to the patient in up to four unit doses per day, each unit dose delivering to the patient 4.5 µg formoterol fumarate dihydrate and 160 µg budesonide.

8. The method of claim 1, wherein the composition is administered to the patient in one or two unit doses per day, each unit dose delivering to the patient 9 µg formoterol fumarate dihydrate and 320 µg budesonide.

9. The method of claim 1, wherein the composition is in the form of a dry powder and is administered from a dry powder inhaler.

10. The method of claim 1, wherein the composition comprises a propellant and is administered from a pressurized metered dose inhaler.

11. The method of claim 1, wherein the composition is administered via a nebulizer.

12. The method of claim 1, wherein the formoterol fumarate dihydrate and budesonide are in the form of particles of a size less than 10 µm.

13. The method of claim 2, wherein the composition comprises a propellant and is administered from a pressurized metered dose inhaler.

14. The method of claim 3, wherein the composition comprises a propellant and is administered from a pressurized metered dose inhaler.

15. The method of claim 4, wherein the composition comprises a propellant and is administered from a pressurized metered dose inhaler.

16. The method of claim 5, wherein the composition comprises a propellant and is administered from a pressurized metered dose inhaler.

17. The method of claim 6, wherein the composition comprises a propellant and is administered from a pressurized metered dose inhaler.

18. The method of claim 7, wherein the composition comprises a propellant and is administered from a pressurized metered dose inhaler.

19. The method of claim 8, wherein the composition comprises a propellant and is administered from a pressurized metered dose inhaler.

20. The method of claim 12, wherein the composition comprises a propellant and is administered from a pressurized metered dose inhaler.

* * * * *